United States Patent
Swanson et al.

(10) Patent No.: US 10,124,115 B2
(45) Date of Patent: Nov. 13, 2018

(54) PUSH BUTTON SAFETY INJECTOR

(71) Applicant: Antares Pharma, Inc., Ewing, NJ (US)

(72) Inventors: Kevin David Swanson, Plymouth, MN (US); Julius Sund, Plymouth, MN (US); Peter A. Hoeft, Seattle, WA (US); Patrick E. Madsen, Litchfield, MN (US)

(73) Assignee: ANTARES PHARMA, INC., Ewing, NJ (US)

( * ) Notice: Subject to any disclaimer, the term of this patent is extended or adjusted under 35 U.S.C. 154(b) by 396 days.

(21) Appl. No.: 14/774,064

(22) PCT Filed: Mar. 12, 2014

(86) PCT No.: PCT/US2014/023862
§ 371 (c)(1),
(2) Date: Sep. 9, 2015

(87) PCT Pub. No.: WO2014/164943
PCT Pub. Date: Oct. 9, 2014

(65) Prior Publication Data
US 2016/0015897 A1  Jan. 21, 2016

Related U.S. Application Data

(60) Provisional application No. 61/779,559, filed on Mar. 13, 2013.

(51) Int. Cl.
*A61M 5/20* (2006.01)
*A61M 5/32* (2006.01)
*A61M 5/30* (2006.01)

(52) U.S. Cl.
CPC ............. *A61M 5/2033* (2013.01); *A61M 5/30* (2013.01); *A61M 5/3202* (2013.01);
(Continued)

(58) Field of Classification Search
CPC ............... A61M 5/326; A61M 5/2033; A61M 2005/2026; A61M 2005/2073;
(Continued)

(56) References Cited

U.S. PATENT DOCUMENTS

2002/0045866 A1*  4/2002  Sadowski ............... A61M 5/20
604/208
2005/0101919 A1  5/2005  Brunnberg
(Continued)

FOREIGN PATENT DOCUMENTS

EP  2364741 A1  9/2011
JP  2002-522171  7/2002
(Continued)

OTHER PUBLICATIONS

Office Action dated Oct. 11, 2016 for Canadian Patent Application No. 2,903,484, 5 pages.
(Continued)

*Primary Examiner* — Nathan R Price
*Assistant Examiner* — Anh Bui
(74) *Attorney, Agent, or Firm* — Morgan, Lewis & Bockius LLP

(57) ABSTRACT

A push button safety injector includes a housing having a proximal end, a distal end spaced from the proximal end, and a longitudinal axis. An injection ram is positioned along the longitudinal axis and configured to actuate a fluid chamber. The injection ram is biased toward the distal end in an initial position. A sliding member is configured to retain the injection ram in the initial position. A safety member confines radial movement of the sliding member in the initial position and allows radial movement of the sliding member in an armed position. A button is moveable between an initial extended position and a depressed position. The button is engagable with the sliding member and configured
(Continued)

to move the sliding member radially in the armed position. The sliding member releases the injection ram when the button is in the depressed position.

20 Claims, 15 Drawing Sheets

(52) U.S. Cl.
CPC ........... *A61M 5/3204* (2013.01); *A61M 5/326* (2013.01); *A61M 2005/206* (2013.01); *A61M 2005/208* (2013.01); *A61M 2005/2026* (2013.01); *A61M 2005/2073* (2013.01); *A61M 2005/3247* (2013.01); *A61M 2005/3267* (2013.01)

(58) Field of Classification Search
CPC .... A61M 2005/208; A61M 2005/3267; A61M 2005/3247; A61M 2005/206
See application file for complete search history.

(56) References Cited

U.S. PATENT DOCUMENTS

| | | | |
|---|---|---|---|
| 2006/0106362 A1* | 5/2006 | Pass | A61M 5/30 604/504 |
| 2006/0270984 A1 | 11/2006 | Hommann | |
| 2010/0198164 A1 | 8/2010 | Kakiuchi | |
| 2013/0018313 A1* | 1/2013 | Kramer | A61M 5/2033 604/131 |

FOREIGN PATENT DOCUMENTS

| | | |
|---|---|---|
| JP | 2005-535415 | 11/2005 |
| JP | 2006-504482 | 2/2006 |
| JP | 2009533124 | 9/2009 |
| JP | 2010-172618 | 8/2010 |
| JP | 2011513035 | 4/2011 |
| WO | 0009186 A2 | 2/2000 |
| WO | 2004016303 A1 | 2/2004 |
| WO | 2004/041331 A1 | 5/2004 |
| WO | 2004041331 A1 | 5/2004 |
| WO | 2009081133 A1 | 7/2009 |
| WO | 2010146358 A2 | 12/2010 |
| WO | 2012073032 A1 | 6/2012 |

OTHER PUBLICATIONS

Extended European search report dated Oct. 11, 2016 for European Patent Application No. 14779472.1, 7 pages.
Office Action for Japanese Patent Application No. 2016-501367.
Office Action dated Jul. 28, 2017 for Canadian Patent Application No. 2,903,484, 3 pages.
International Search Report and Written Opinion for PCT/US14/23862 dated Aug. 11, 2014.

* cited by examiner

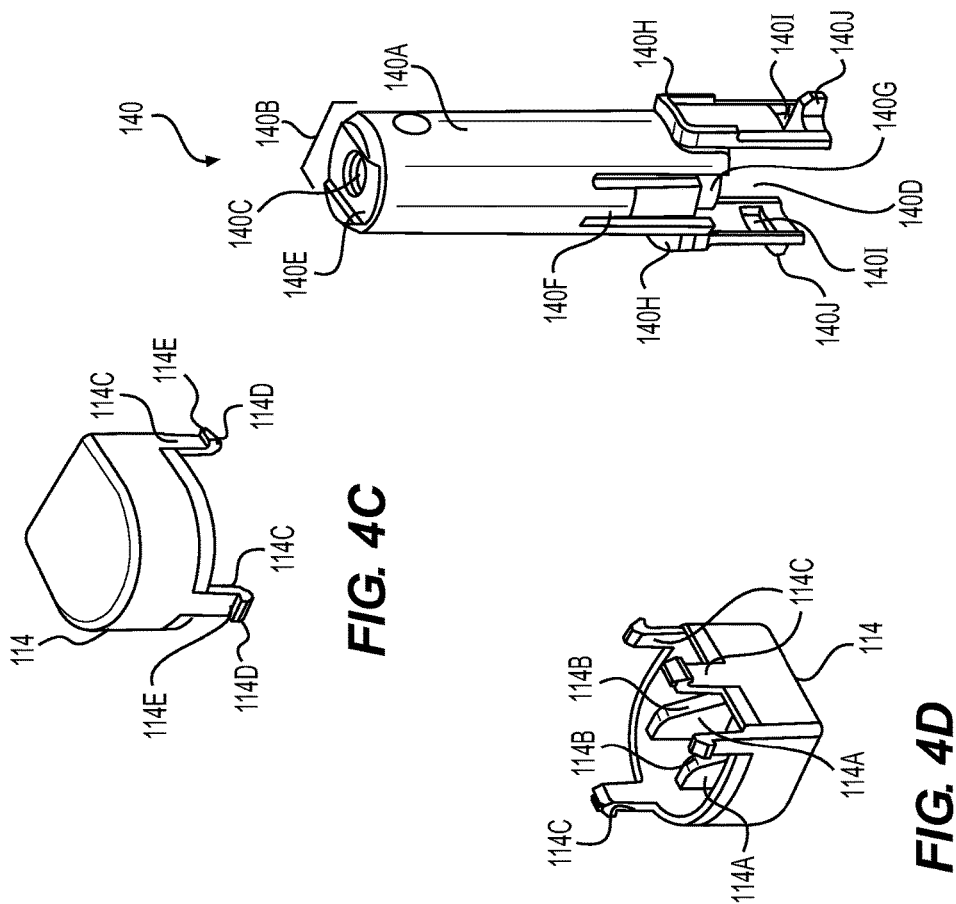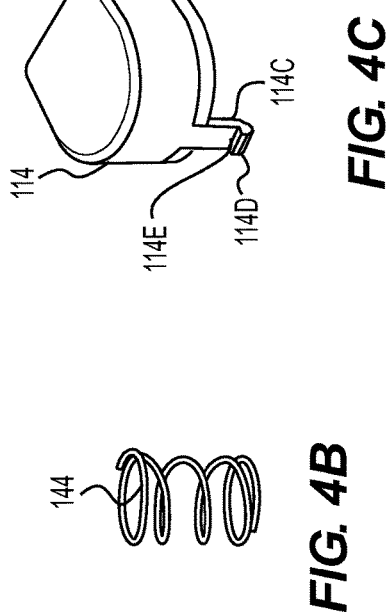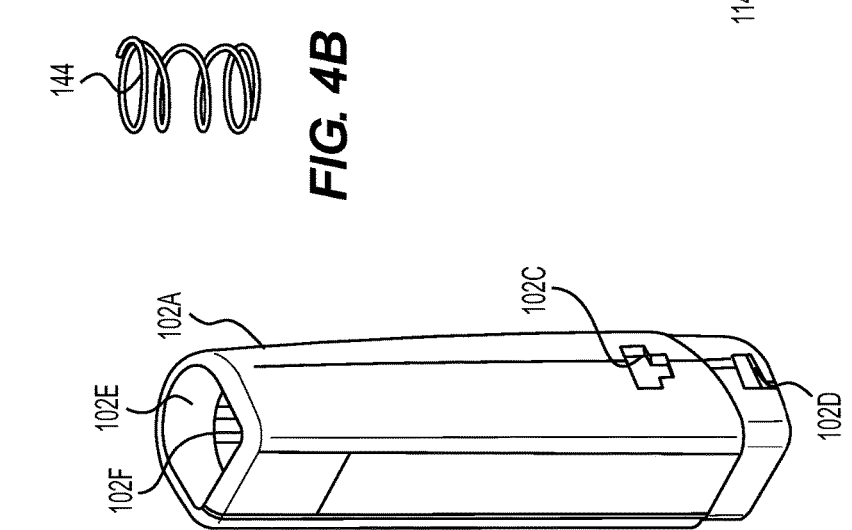

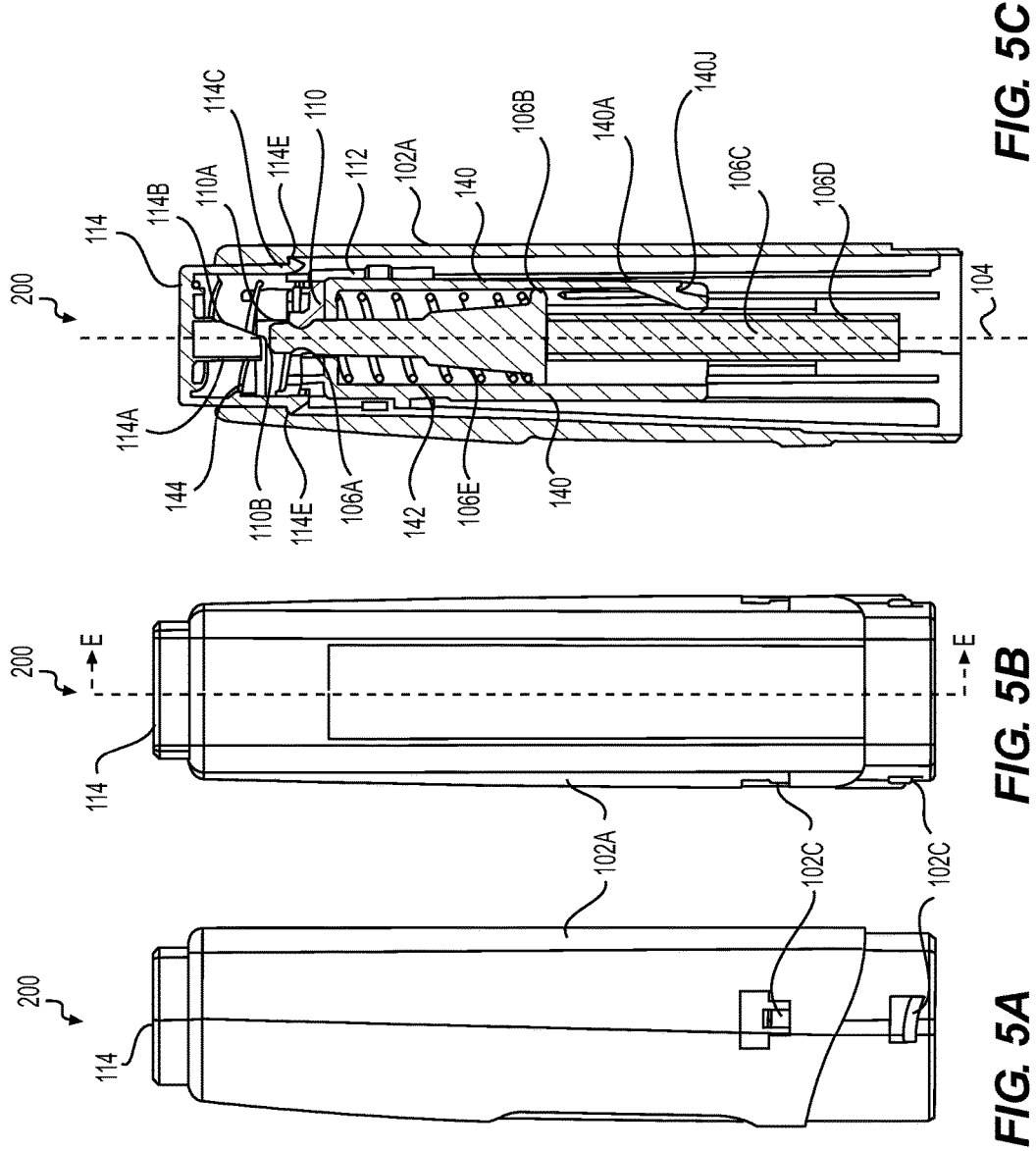

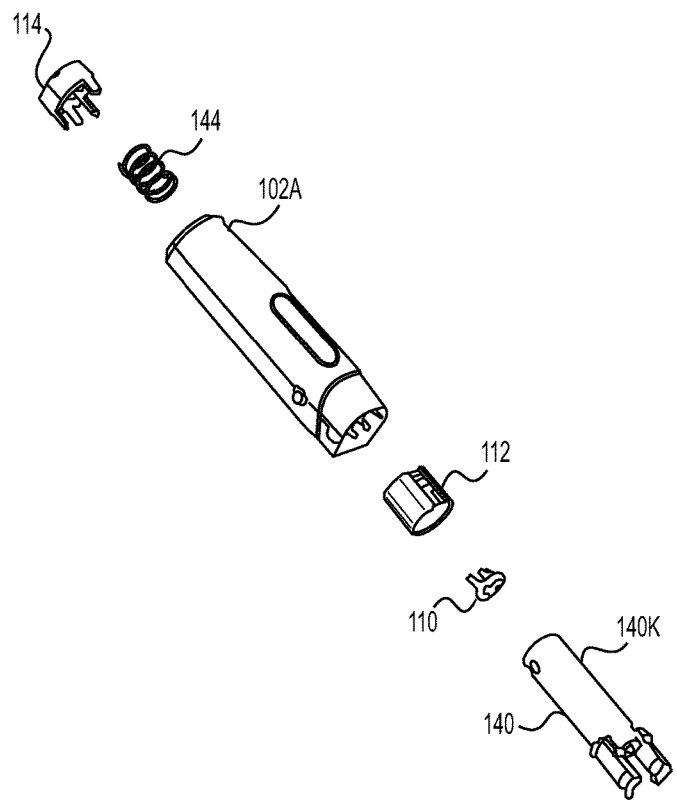
FIG. 6
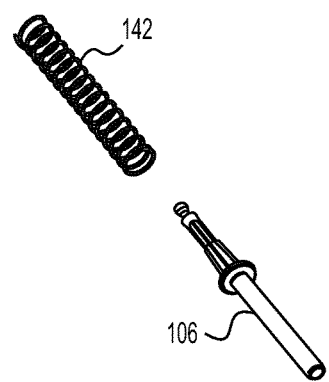

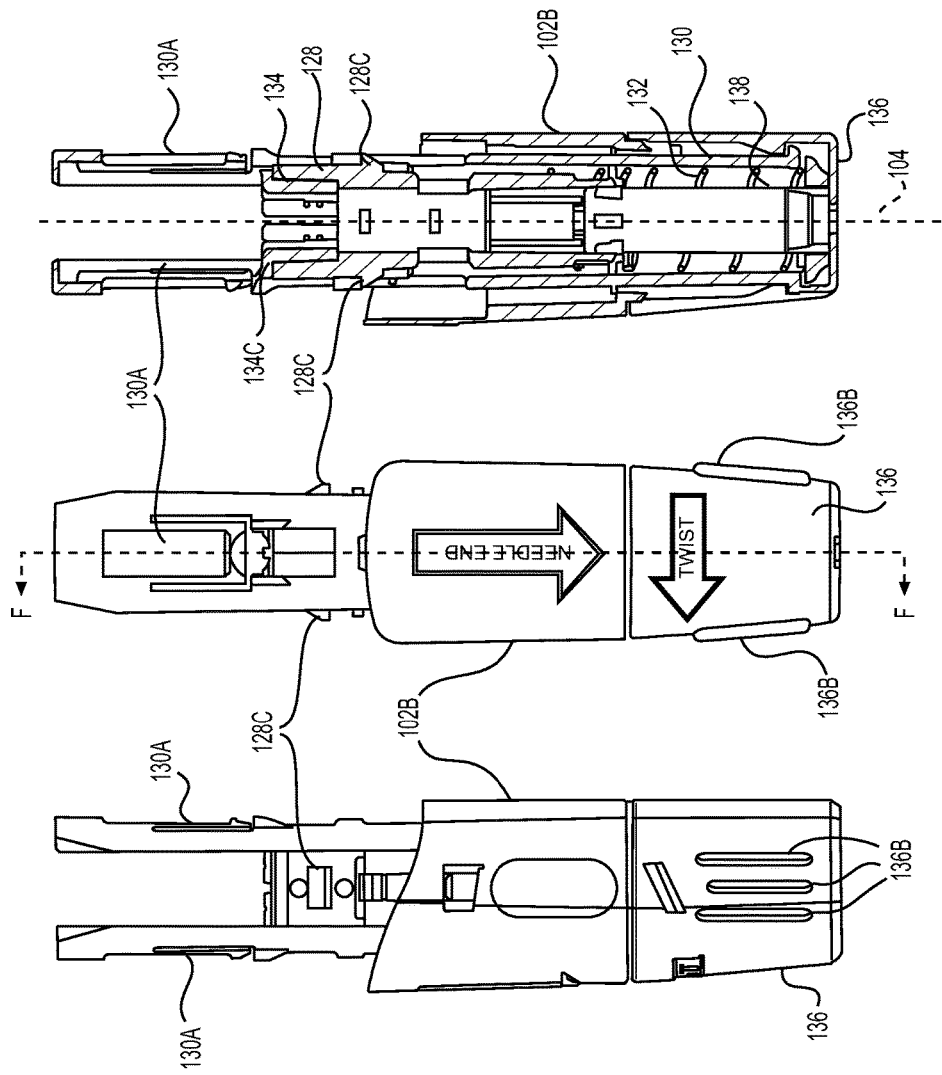

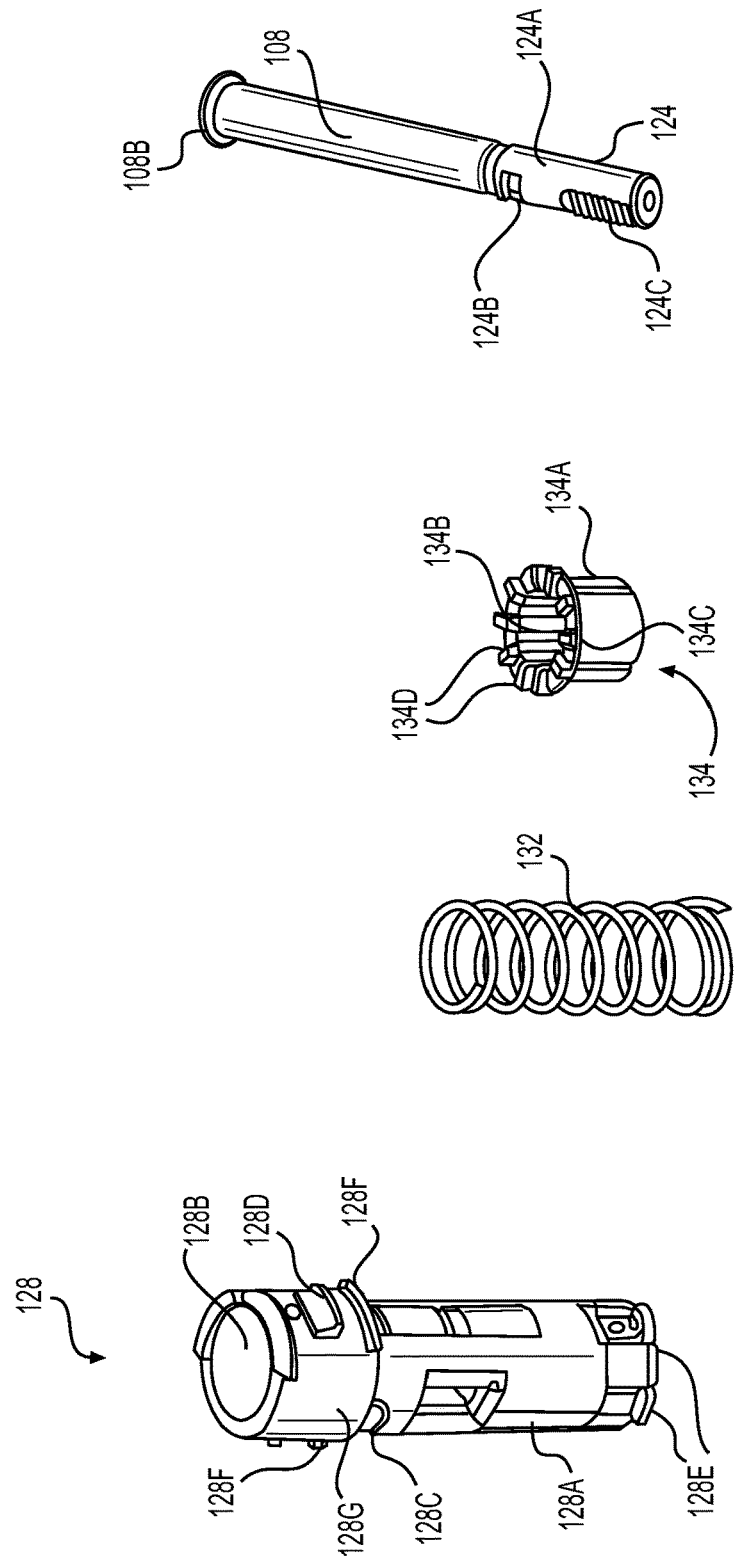

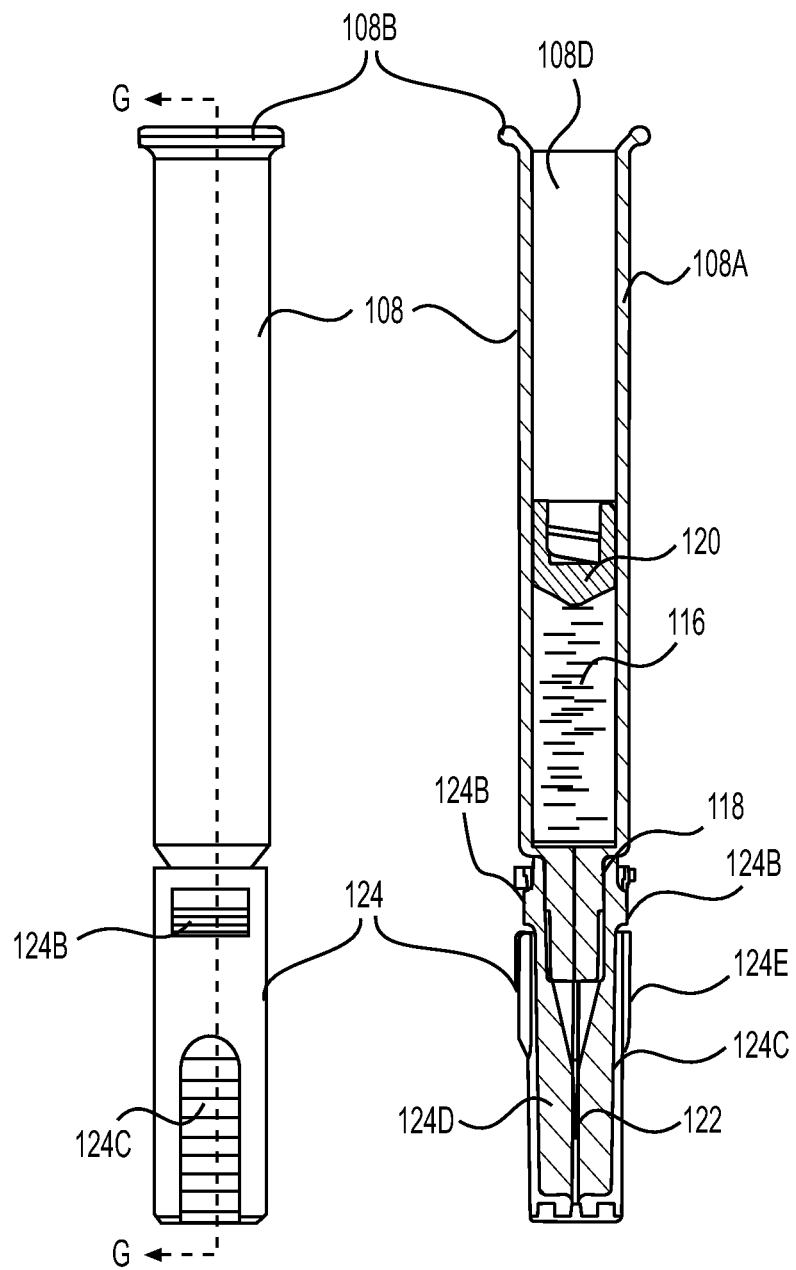
FIG. 10A  FIG. 10B

PUSH BUTTON SAFETY INJECTOR

CROSS-REFERENCE TO RELATED APPLICATIONS

This application is a U.S. National Stage Entry of International Patent Application PCT/US2014/023862, filed on Mar. 12, 2014, which in turn claims the benefit of U.S. Provisional Patent Application No. 61/779,559 filed Mar. 13, 2013 entitled "Push Button Safety Injector", which are incorporated by reference herein in their entirety.

FIELD OF THE INVENTION

The present invention relates to a push button safety injector.

BRIEF SUMMARY OF THE INVENTION

In one embodiment there is a push button safety injector comprising: a housing having a proximal end, a distal end spaced from the proximal end, and a longitudinal axis; an injection ram positioned along the longitudinal axis and configured to actuate a fluid chamber, the injection ram being biased toward the distal end in an initial position; a sliding member retaining the injection ram in the initial position; a safety member confining radial movement of the sliding member in the initial position and allowing radial movement of the sliding member in an armed position; and a button moveable between an initial extended position and a depressed position, the button being engagable with the sliding member and configured to move the sliding member radially in the armed position, wherein the sliding member releases the injection ram when the button is in the depressed position.

In a further embodiment, the push button safety injector comprises the fluid chamber, the fluid chamber configured for storing and dispensing a liquid medicament through an injection outlet. In one embodiment, the fluid chamber includes a piston slidably and sealingly received there within and configured to be longitudinally movable in the fluid chamber. In one embodiment, the fluid chamber includes an injection outlet. In a further embodiment, the push button safety injector comprises a retractable needle guard configured to be moveable longitudinally relative to the fluid chamber between an extended position, in which it extends along at least a length of the injection outlet, and a retracted position, in which the retractable needle guard exposes at least a portion of the length of the injection outlet. In a further embodiment, the push button safety injector comprises a sleeve member interposed between the fluid chamber and the retractable needle guard. In one embodiment, the retractable needle guard is biased toward the distal end of the housing in the extended position. In one embodiment, the injection outlet comprises a hollow injection needle configured for piercing through a user's skin and for delivering a needle-assisted jet of a medicament contained in the fluid chamber. In one embodiment, the fluid chamber includes a prefilled syringe or carpule configured to fit within the housing.

In a further embodiment, the push button safety injector comprises a sleeve member configured to hold and position the fluid chamber and/or to minimize movement of the fluid chamber due to injection force of the injection ram. In one embodiment, the sleeve member is contained within and mounted to the housing and configured to act as a support for a biasing member interposed between the sleeve member and the needle guard. In a further embodiment, the push button safety injector comprises an elastomeric member interposed between the fluid chamber and the sleeve member. In one embodiment, the sliding member includes an aperture extending longitudinally there through. In one embodiment, the aperture includes a slot and a hole, wherein the slot is in communication with the hole. In one embodiment, the slot has a width and the hole has a diameter, wherein the width of the slot is less than the diameter of the hole. In one embodiment, the injection ram near the proximal end includes an engagement recess configured to engage the slot of the sliding member when the injection ram is in the initial position and to be slidably disengagable from the slot when the safety member is in the armed position.

In a further embodiment, the push button safety injector comprises a safety cap removably coupled to the distal end of the housing, wherein a user must first remove the safety cap from the housing before the user can place the safety member in the armed position. In one embodiment, the safety cap removably is configured to receive proximal end of the retractable needle guard there within. In a further embodiment, the push button safety injector comprises a lock-out mechanism having at least one flexible arm formed in the supporting member and at least one slot formed in the retractable needle guard, the flexible arm being configured to be moveable between an initial unlocked position, which allows longitudinal movement of the needle guard relative to the supporting member, and a lock-out position, in which the at least one flexible arm is in a locking engagement with the at least one slot of the retractable needle guard, wherein the retractable needle guard is locked in the extended position following injection. In one embodiment, the safety member is moved relative to the sliding member between the initial position and the armed position.

BRIEF DESCRIPTION OF THE SEVERAL VIEWS OF THE DRAWINGS

The following detailed description of embodiments of the push button safety injector, will be better understood when read in conjunction with the appended drawings of an exemplary embodiment. It should be understood, however, that the invention is not limited to the precise arrangements and instrumentalities shown. It is noted that, in the context of this disclosure, the terms "distal" and "proximal" are used in reference to the position of injection device 100 relative to a user of the injection device when merely held by a user. Accordingly, a point located distal to a second point would be further from the user (e.g., towards an injection end of injection device 100) and vice versa.

In the drawings:

FIG. 4A is a prospective top view of a proximal housing part of the push button safety injector of FIG. 1;

FIG. 4B is a perspective side view of a button spring of the biasing member of the push button safety injector shown in FIG. 1;

FIG. 4C is a perspective top view of a push button of the push button safety injector shown in FIG. 1;

FIG. 4D is a perspective bottom view of the push button of the push shown in FIG. 4C;

FIG. 4E is a perspective top view of a supporting member of the push button safety injector shown in FIG. 1;

FIG. 5A is a side view of a first subassembly (Module A) of the push button safety injector shown in the exploded view of the push button safety injector in FIG. 3;

FIG. 5B is a back side view of the first subassembly (Module A) of the push button safety injector as shown in the exploded view of the push button safety injector in FIG. 3;

FIG. 5C is a cross-section view of the first subassembly (Module A) of the push button safety injector shown FIG. 5C taken along the line E-E;

FIG. 6 is a an exploded front view of the first subassembly (Module A) of the push button safety injector of FIG. 5A;

FIG. 7A is a side view of a second subassembly (Module B) of the push button safety injector as shown in the exploded view of the push button safety injector shown in FIG. 3;

FIG. 7B is a front side view of the second subassembly (Module B) of the push button safety injector as shown in FIG. 7A;

FIG. 7C is a cross-section view of the second subassembly (Module B) of the push button safety injector of FIG. 7B taken along line F-F;

FIG. 8A is a perspective top view of a sleeve member of the push button safety injector shown in FIG. 1;

FIG. 8B is a perspective view of a return spring as a biasing member of retractable needle guard of the push button safety injector shown in FIG. 1;

FIG. 8C is a perspective top view of a elastomeric member of the push button safety injector shown in FIG. 1;

FIG. 8D is a perspective front view of a third subassembly (Module C) of the push button safety injector as shown in the exploded view of the push button safety injector shown in FIG. 3;

FIG. 10A is a front view a third subassembly (Module C) of the push button safety injector shown in FIG. 3;

FIG. 10B is a cross-sectional view of the third subassembly (Module C) shown in FIG. 10A;

DETAILED DESCRIPTION OF THE INVENTION

Figure 1:
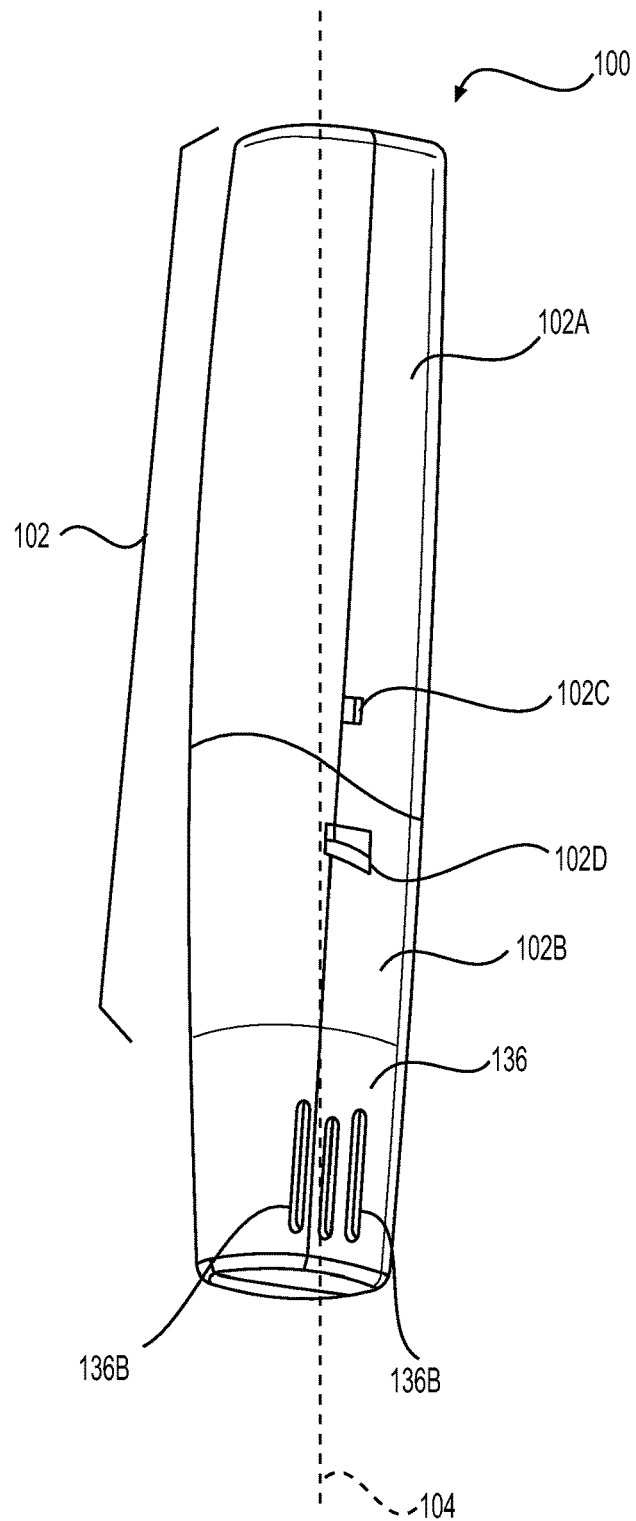
FIG. 1 is a perspective view of an exemplary embodiment of a push button safety injector having an injection system according to the present invention.

Referring to the drawings in detail, wherein like reference numerals indicate like elements throughout, there is shown in FIGS. 1-13C a push button safety injector, generally designated with reference numeral 100, for safe injection of a liquid medicament into a patient in accordance with exemplary embodiments of the present invention.

Push button safety injectors are highly desirable whether they are of the configuration that use a needle and syringe or are of needleless configuration. Attributes that are highly desirable in push button safety injectors include accuracy in metering a dose of the medication to be administered, consistency of administered dose of medication from injection to injection and/or precise variation of dose from injection to injection. It is also highly desirable that push button safety injectors be capable of use not only by the patients themselves, but also be usable even by someone with limited physical capabilities. For example, physically disabled patients are often in need of regular medication. Some patients have particular difficulty with motor control, and yet to live an independent life, they need to be able to self-administer injections. Needleless injector or needle-assisted injectors with appropriate safety mechanisms are especially suitable for these types of patients as well as for other patients without disabilities. It is also desirable that push button safety injectors be used to safely administer medication and to be safely disposed by one who has had no medical training and who has had little training or experience in the use of push button safety injectors in general.

In some embodiments, the push button safety injector according to the present invention is a jet injector. In one embodiment, the push button safety injector of the present invention is configured to rapidly deliver a medication as a fluid jet. In one embodiment, the push button safety injector is configured to produce a distally directed actuation force that is sufficiently powerful to expel a fluid jet of medication stored in a fluid chamber coupled thereto as fluid jet capable of piercing the skin of a patient and deliver the medication subcutaneously to an injection depth. In one embodiment, the push button safety injector of the present invention is configured to jet inject medication in fractions of a second.

In one embodiment, the push button safety injector typically uses a high-pressure narrow jet of an injectable medicament instead of a hypodermic needle to penetrate the skin of a patient. The absence of a hypodermic needle provides a psychological benefit that is conducive to medication compliance. This is important because medication non-compliance by patients is a major obstacle to effective delivery of health care. In an alternative embodiment, the push button safety injector includes a hypodermic needle. In one embodiment, the push button safety injector is configured to advantageously to exploit the psychological benefit of a concealed injection needle. In one embodiment, the push button safety injector is configured to include a retractable needle guard which hides the injection needle in extended position and exposes the injection needle in a retracted injection.

In some exemplary embodiments, the push button safety injector can include a housing having a longitudinal axis. In one embodiment, the housing has peripheral dimensions configured to facilitate ease of and convenience of carrying, handling and/or using the push button safety injector. In one embodiment, the housing is formed of proximal and distal mating parts configured to join to one another. In one embodiment, the proximal and distal mating parts of the housing are configured to be joined by a snap fit, a press fit, or by adhesives or welding. In one embodiment, the push button safety injector includes an injection ram positioned along the longitudinal axis of the housing. In one embodiment, the injection ram is configured to be movable along the longitudinal axis between an initial position and a fired position. In one embodiment, the push button safety injector includes a sliding member configured to retain the injection ram in the initial position. In one embodiment, the push button safety injector includes a safety member confining radial movement of the sliding member in the initial position and allowing radial movement of the sliding member in an armed position. In one embodiment, the push button safety injector includes a button moveable relative to the housing between an initial extended position and a depressed position. In one embodiment, the button is configured to engage the sliding member and move it radially in the armed position. In one embodiment, the sliding member is configured to release the injection ram in the depressed position of the button.

In some embodiments, the housing of the push button safety injector is configured to contain internal components of the push button safety injector. In one embodiment, at least some internal components of the push button safety injector are arranged along the longitudinal axis of the housing. In one embodiment, the internal components of the push button safety injector include a supporting member positioned coaxially within the housing. In one embodiment, the supporting member is positioned coaxially within the proximal mating part of the housing. In one embodiment, the supporting member is configured to provide support for one or more internal components of the push button safety injector. In one embodiment, the supporting member is configured to position an injection ram. In one embodiment, the supporting member is configured to provide support to a sliding member of the push button safety injector. In one embodiment, the supporting member is configured to be slidably received in a safety member of the push button safety injector. In one embodiment, the supporting member is configured to cooperate with the sliding member to facilitate biasing of the injection ram toward the distal end of the housing of the push button safety injector. In one embodiment, the supporting member is configured to provide a surface against which the sliding member can slide laterally when the safety member is in an armed position.

Generally, in an exemplary embodiment, a push button safety injector of the present invention is designed to be lightweight and yet physically robust to withstand physical impact of a fall or a drop onto a hard surface from a certain height with minimum risk of unintended firing of the push button safety injector. In some embodiments, the push button safety injector is provided in a locked state in which neither the button nor the sliding member can be moved until the push button safety injector is readied for firing by a user of the push button safety injector. In one embodiment, in order for the push button safety injector to be readied for injection, a user of the push button safety injector must first cause a needle guard to move longitudinally relative to the supporting member in the proximal direction. In one embodiment, the user can cause the retractable needle guard to move from its initial extended position to a retracted position. In one embodiment, the user actuates the push button safety injector to introduce injection needle at an injection site.

Generally, once the safety member is in the armed position, the push button safety injector is ready for firing. A user of the push button safety injector can then either fire the push button safety injector by actuating an injection button or disarm the safety member and therefore abort firing of the injector. In one embodiment, the user disarms the safety by allowing the needle guard to return to its initial extended position. In one embodiment, return of the needle guard to its initial extended position causes the safety member to move axially relative to the supporting member in the distal direction.

In some embodiments, movement of the needle guard between its initial extended position and its retracted position also causes longitudinal movement of a safety member between the initial position and the armed position. In one embodiment, the safety member has a proximal end in contact relation with the proximal end of the supporting member in the initial position. In one embodiment, the safety member has a proximal end in spaced relation with the proximal end of the supporting member in the armed position. In one embodiment, the safety confines lateral movement of a sliding member when in contact relation with the supporting member. In another embodiment, the safety member allows lateral movement of the sliding member when in the spaced relation with the supporting member.

Figure 2A:
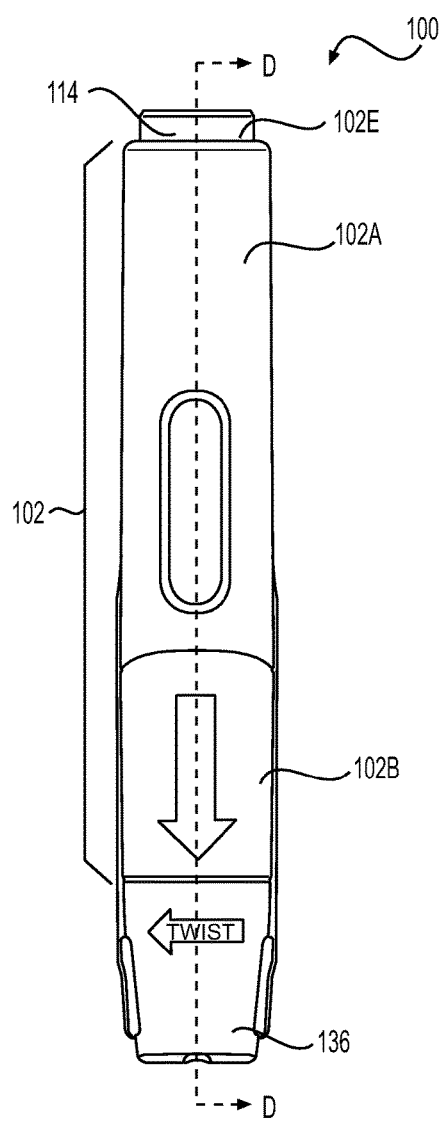
FIG. 2A is a front view of the push button safety injector shown in FIG. 1.
Figure 2B:
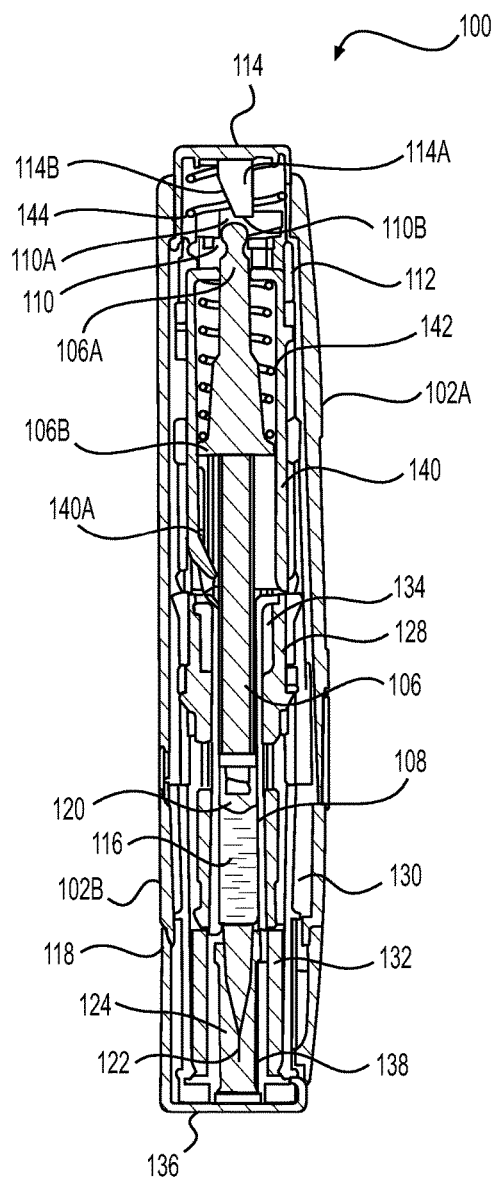
FIG. 2B is a cross-sectional view of the push button safety injector of FIG. 2A taken along line D-D.

Referring to FIGS. 1-2B, in an exemplary embodiment, push button safety injector 100 includes a housing 102 having a longitudinal axis 104. In one embodiment, push button safety injector 100 includes an injection ram 106 positioned along longitudinal axis 104 of housing 102 and configured to actuate a fluid chamber 108. In one embodiment, injection ram 106 is biased toward distal end of housing 102 in an initial position. In one embodiment, push button safety injector 100 includes a sliding member 110 configured to retain injection ram 106 in the initial position. In one embodiment, push button safety injector 100 includes a safety member 112 configured to confine radial movement of sliding member 110 in the initial position. In one embodiment, safety member 112 is configured to allow radial movement of sliding member 110 in an armed position. In one embodiment, push button safety injector 100 includes a push button 114 moveable between an initial extended position and a depressed position. In one embodiment, button 114 is configured to be engagable with sliding member 110 and to move sliding member 110 laterally or radially in the armed position, wherein sliding member 110 releases injection ram 106 in the depressed position.

Referring to FIG. 1, in one embodiment, push button safety injector 100 comprises an elongate housing 102. In one embodiment, housing 102 includes a proximal end and a distal end and a longitudinal axis 104 extending along the length of housing 102 from the proximal end to the distal end of housing 102. In one embodiment, housing 102 comprises two mating housing parts 102A and 102B. In one embodiment, housing part 102A and housing part 102B are joined by snap fitting at least one tab 102D on housing part 102A that engages at least one slot in housing part 102B. In other embodiments, housing part 102A and housing part 102B are integral or joined by any preferred manner, such as a press fit, adhesives, or welding. In one embodiment, safety cap 136 is coupled to the distal end of housing 102. In one embodiment, safety cap 136 includes a set of ribs 136B configured to increase friction between a user's fingers and outer peripheral surface of safety cap 130 to facilitate removal of safety cap 136 by the user.

Referring to FIG. 2A, in one embodiment, housing 102 includes an axial opening 102E at its proximal end. In one embodiment, push button 114 is moveably received in axial opening 102E of housing 102 and configured to be moveable relative to housing 102 between an extended position and a depressed position.

Referring to FIGS. 2B, 4C, and 4D, in one embodiment, push button safety injector 100 includes push button 114 having at least one ramped member 114A (see FIG. 4D) extending longitudinally into the interior of housing 102A. In one embodiment, at least one ramped member 114A includes a ramped surface 114B. In one embodiment, ramped surface 114B is at an oblique angle relative to longitudinal axis 104. In one embodiment, at least one ramped member 114A is configured to be operatively associated with sliding member 110. In one embodiment, push button 114 includes at least one leg 114C having near its distal end a protrusion 114D projecting radially outward. In one embodiment, protrusion 114D of the at least one leg 114C includes a proximal facing surface 114E. In one embodiment, the at least one leg 114C of push button 114 is configured to engage circumferential undercut 102F in inner peripheral surface of housing 102. In one embodiment, protrusion 114D of the at least one leg 114C is configured to retain push button 114 in housing 102.

Figure 4I:
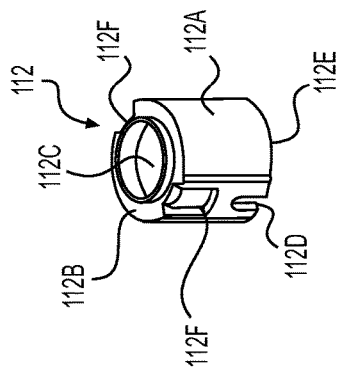
FIG. 4I is a perspective top view of a safety member of the push button safety injector shown in FIG. 1.
Figure 4J:
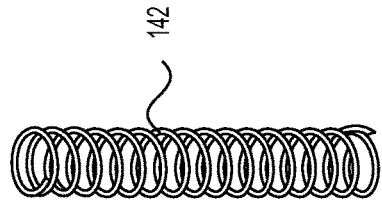
FIG. 4J is a perspective top view of a main spring as a biasing member of the injection ram of the push button safety injector shown in FIG. 1.
Figure 4G:
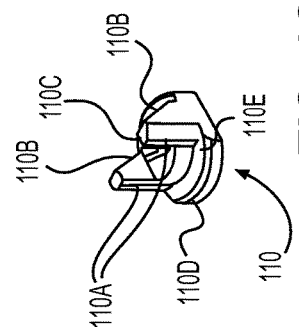
FIG. 4G is a perspective top view of a sliding member of the push button safety injector of FIG. 1.
Figure 4H:
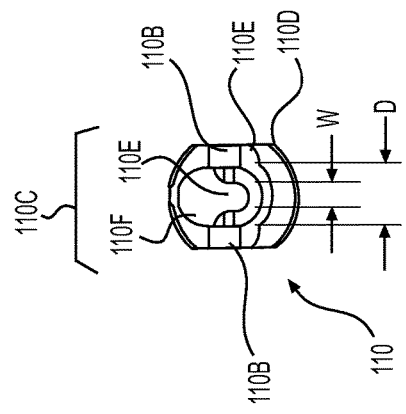
FIG. 4H is a perspective front view of the sliding member of FIG. 4G.

Referring to FIGS. 2B, 4G and 4H, in one embodiment, sliding member 110 includes at least one ramped member 110A extending axially toward the distal end of housing 102. In one embodiment, at least one ramped member 110A is configured to be complementary with at least one ramped member 114A (see FIGS. 4C and 4D). In one embodiment, at least one ramped member 110A includes a ramped surface 110B. In one embodiment, ramped surface 110B angled relative to longitudinal axis 104. In one embodiment, ramped surface 110B is angled to complement ramped surface 114B of push button 114. In one embodiment, ramped surface 110B is complementary with ramped surface 114B. In one embodiment, ramped surface 110B is configured to be engageable with ramped surface 114B.

Referring to FIG. 2B, in one embodiment, sliding member 110 is actuated by axial movement of push button 114. In one embodiment, push button 114 is moveable between an initial extended position and a depressed position (see FIG. 13C), wherein push button 114 is engageable with sliding member 110 to move sliding member 110 radially when safety member 112 is in an armed position. In one embodiment, sliding member 110 is configured to retain injection ram 106 when push button 114 is in the initial extended position. In one embodiment, sliding member 110 is configured to release injection ram 106 when push button 114 is in the depressed position. In one embodiment, ramped member 114A of push button 114 is configured to be longitudinally shiftable so as to engage ramped member 110A. In one embodiment, ramped surface 114B of ramped member 114 is configured to engage ramped surface 110B of sliding member 110 (see FIG. 13C) to cause sliding member 110 to move radially or laterally with respect to longitudinal axis 104 as push button 114 is moved from the extended position to the depressed position when safety member 112 is in the armed position.

Referring to FIGS. 2B and 4E, in one embodiment, push button safety injector 100 includes supporting member 140, supporting member 140 configured to support one or more internal components of push button safety injector 100. In one embodiment, supporting member 140 includes a body 140A having a proximal end surface 140B with a hole 140C extending longitudinally through it, and an axial opening 140D at its distal end. In one embodiment, body 140A of supporting member 140 is hollow. In one embodiment, body 140A of supporting member 140 is configured to slidably receive and position injection ram 106 there within. In one embodiment, end surface 140B of supporting member 140 defines a laterally extending receiving channel 140E. In one embodiment, body 140A of supporting member 140 includes at least one flexible arm 140F formed therein, the at least one flexible arm 140F configured to be deflectable radially away from longitudinal axis 104 b injection ram 106 is released by sliding member 110. In one embodiment, at least one flexible arm 140F extends longitudinally to the distal edge of body 140A of supporting member 140. In one embodiment, the at least one flexible arm 140F includes a stepped engaging portion 140G near its distal end.

Referring to FIGS. 2B and 4E, in some embodiments, supporting member 140 includes at least one axial leg 140H extending longitudinally along outer peripheral surface of body 140A from a point near distal end of body 140 to a predetermined length (distance) beyond the distal end of body 140A. In one embodiment, at least one axial leg 140H includes a slot 140I there through near its distal end. In one embodiment, at least one axial leg 140H includes a protrusion 140J extending radially away from longitudinal axis 104. In one embodiment, protrusion 140J is located at the distal end of at least one axial leg 140H.

Referring to FIG. 4E, in one embodiment, supporting member 140 includes a pair of axial legs 140H. In one embodiment, supporting member 140 includes a pair of axial legs 140H arranged at non-symmetrically spaced locations along the outer peripheral surface of body 140A of supporting member 140. In one embodiment, supporting member 140 is secured within housing 102 by snap fitting protrusion 140J on at least one axial leg 140H into a slot 102C (see FIGS. 3 and 4A) in housing part 102A.

Referring to FIGS. 2B, 4E, and 4G, in one embodiment, supporting member 140 is configured to provide support for one or more internal components of push button safety injector 100. In one embodiment, supporting member 140 is configured to receive sliding member 110 on its end surface 140B. In one embodiment, receiving channel 140C of supporting member 140 is configured to receive distal end of sliding member 110 therein. In one embodiment, receiving channel 140C of supporting member 140 is configured to guide distal end of sliding member 110 during lateral movement of sliding member 110.

Figure 4F:
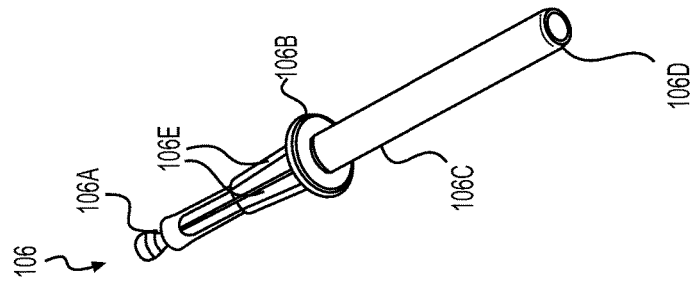
FIG. 4F is a perspective front view of an injection ram of the push button safety injector shown in FIG. 1.

Referring to FIGS. 2B, 4E, and 4F, in one embodiment, supporting member 140 is configured to provide support for one or more internal components of push button safety injector 100. In one embodiment, supporting member 140 is configured to slidably position injection ram 106 within its body 140A along longitudinal axis 104. In one embodiment, supporting member 140 is configured to slidably receive a substantially length of injection ram 106 within its body 140A such that proximal end of injection ram 106 extends through axial hole 140C.

Referring to FIGS. 2B, 4G, 4F, and 4H, in one embodiment, injection ram 106 includes a recess 106A near its proximal end, recess 106A configured to aperture 110C in sliding member 110. In one embodiment, injection ram 106 includes a longitudinally extending stem 106C configured to be slidably received within fluid chamber 108. In one embodiment, injection ram 106 includes a radially enlarged rib or collar 106B formed on its peripheral surface at the proximal end of longitudinal stem 106C. In one embodiment, injection ram 106 includes a plurality of longitudinally elongated fins 106E radially extending from its outer peripheral surface between recess 106A and radially enlarged rib 106B. In one embodiment, plurality of fins 106E has a first diameter adjacent recess 106A and a second diameter adjacent radially enlarged rib 106B, wherein the second diameter is larger than the first diameter.

Referring to FIGS. 4F, 4G, and 4H, in one embodiment, sliding member 110 includes a base member 110D having an aperture 110C extending longitudinally there through. In one embodiment, aperture 110C includes a slot 110E and a hole 110F in communication with slot 110E, wherein width W of slot 110E is less than diameter D of hole 110F. In one embodiment, slot 110E of aperture 110C is configured to engage recess 106A of injection ram 106. In one embodiment, slot 110E of aperture 110C is configured to slidably engage recess 106A of injection ram 106 and hold injection ram 106 in the initial position.

Referring to FIGS. 4E-4J, in one embodiment, sliding member 110 is configured to cooperate with supporting member 140 to facilitate biasing of injection ram 106 toward the proximal end of push button safety injector 100. In one embodiment, base member 110D of sliding member 110 is received in receiving channel 140E of supporting member 140. In one embodiment, injection ram 106 is received within supporting member 140 and through its axial hole 140C and hole 110F of sliding member 110. In one embodiment, recess 106A of injection ram is engaged with slot 110E of sliding member 110. In one embodiment, a biasing member 142 is interposed between radially enlarged rib 106B of injection ram 106 and inner peripheral surface of supporting member 140. In one embodiment, biasing member 142 is configured to provide a biasing force for urging injection ram 106 in the distal direction of push button safety injector 100. In one embodiment, biasing member 142 is biasing a spring, a piston, a flexible member, or a compressible member.

A push button safety injector according to the present invention, in some exemplary embodiments, safeguards against accidental use of the push button safety injector, for example, by preventing unintended triggering and/or firing of the push button safety injector by a user or during shipment or when accidently dropped onto a hard surface. Also, in some embodiments, a push button safety injector according to the present invention can be used in combination with a lock-out mechanism which prevents reuse of the push button safety injector. A push button safety injector of the present invention in combination with a lock-out mechanism can also minimizes exposure of a user of the push button safety injector or others with access to the push button safety injector to the possibility of accidental needle sticks and other risks associated with exposure to residual medicament, bodily fluids, and/or blood borne pathogens during handling and/or disposal of the push button safety injector subsequent to an injection.

Referring to FIGS. 4I and 5C, in one embodiment, safety member 112 includes a body 112A having a hollow interior and outer surface 112B at its proximal end and an axial opening 112E at its distal end, axial opening 112E being in communication with the hollow interior of body 112A. In one embodiment, axial hole 112C of safety member 112 is configured to slidably receive base member 110D of sliding member 110 there through. In one embodiment, axial opening 112E of safety member 112 is dimensioned to allow proximal end of supporting member 140 to be slidably received into the hollow interior of body 112A of safety member 112 includes axial slot 112D extending from a point near the distal end of body 112A of safety member 112 to its distal edge. In one embodiment, axial slot 112D is configured to slidably receive guiding protrusion 140K (see FIG. 6) located on the outer peripheral surface of supporting member 140. In one embodiment, guiding protrusion 140K of supporting member 140 is configured to facilitate instillation of safety member 112 correctly. In one embodiment, guiding protrusion 140K of supporting member 140 is configured to restrict angular rotation of safety member 112 about longitudinal axis 104.

Referring to FIGS. 4I and 5C, in one embodiment, the hollow interior of body 112A of safety member 112 includes inner end surface at the proximal end of safety member 112. In one embodiment, the proximal end of supporting member 140 is in contact relation with the inner surface at the proximal end of safety member 112. In one embodiment, safety member 112 cooperates with supporting member 140 to confine lateral movement of sliding member 110. In one embodiment, lateral movement of sliding member 110 is restricted when the inner surface of the proximal end of safety member 112 is in contact relation with end surface 140B of supporting member 140. In one embodiment, sliding member 110 is laterally moveable when safety member 112 is in spaced relation with end surface 140B of supporting member 140.

Referring to FIGS. 4I, 4C and 4D, in one embodiment, safety member 112 includes at least one axial slot 112F configured to slidably receive therein at least one leg 114C of push button 114. In one embodiment, a biasing member 144 is interposed between outer surface 112B of safety member 112 and push button 114. In one embodiment, a biasing member 144 is configured to provide a biasing force for urging push button 114 along longitudinal axis 104 toward the proximal end of push button safety injector 100. In one embodiment, biasing member 144 is configured to provide a biasing force for urging safety member 112 along longitudinal axis 104 toward the distal end of push button safety injector 100. In one embodiment, biasing member 144 is a spring, a piston, a flexible member, or a compressible member.

Referring to FIGS. 3, 5A-5C, and 6, in some embodiments, push button safety injector 100 is comprised of a plurality of modules or subassemblies. In one embodiment, push button safety injector 100 includes a first subassembly or module A having a plurality of internal components of push button safety injector 100. In one embodiment, push button safety injector 100 (see FIG. 5C) includes housing part 102A and supporting member 140 positioned therein along longitudinal axis 104. In one embodiment, push button safety injector 100 includes injection ram 106 positioned along longitudinal axis 104 within the hollow interior of body 140A of supporting member 140. In one embodiment, push button safety injector 100 includes biasing member 142 configured to provide a biasing force for urging injection ram 106 toward the distal end of housing part 102A in an initial position. In one embodiment, push button safety injector 100 includes sliding member 110 in abutting relation with end surface 140B of supporting member 140. In one embodiment, push button safety injector 100 includes a safety member 112 slidably mounted on the proximal end of supporting member 140. In one embodiment, safety member 112 and supporting member 140 cooperate to confining radial movement of sliding member 110 in the initial position. In one embodiment, push button safety injector 100 includes push button 114 positioned longitudinally along longitudinal axis 104 at the proximal end of housing part 102A. In one embodiment, push button 114 is configured to be moveable between an initial extended position and a depressed position relative to housing part 102. In one embodiment, push button safety injector 100 includes biasing member 144 interposed between push button 114 and safety member 112. In one embodiment, biasing member 144 is configured to provide a biasing force for urging push button 114 in the proximal direction of housing part 102A.

Figure 3:
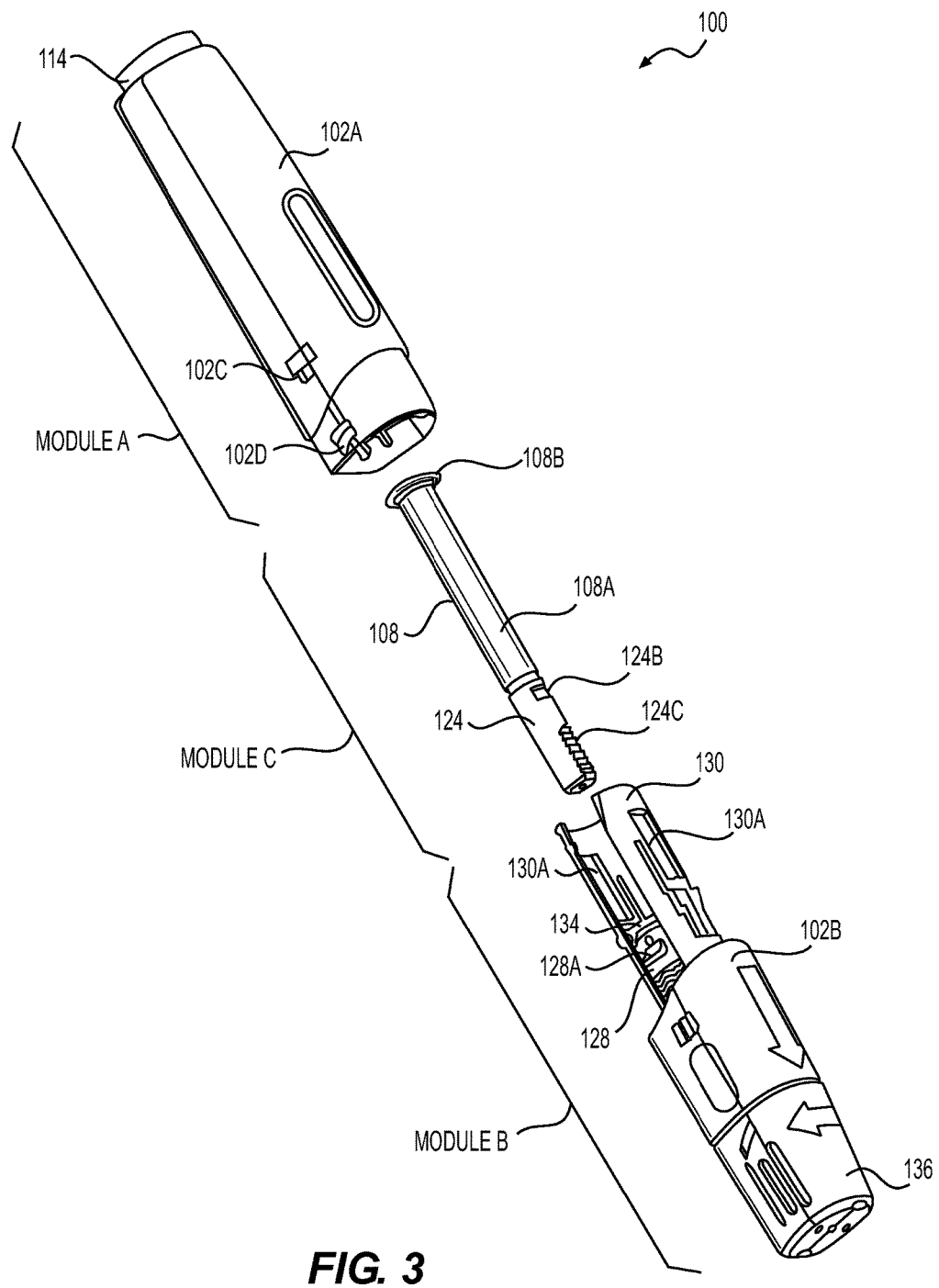
FIG. 3 is an exploded view of the push button safety injector shown in FIG. 1.
Figure 9:
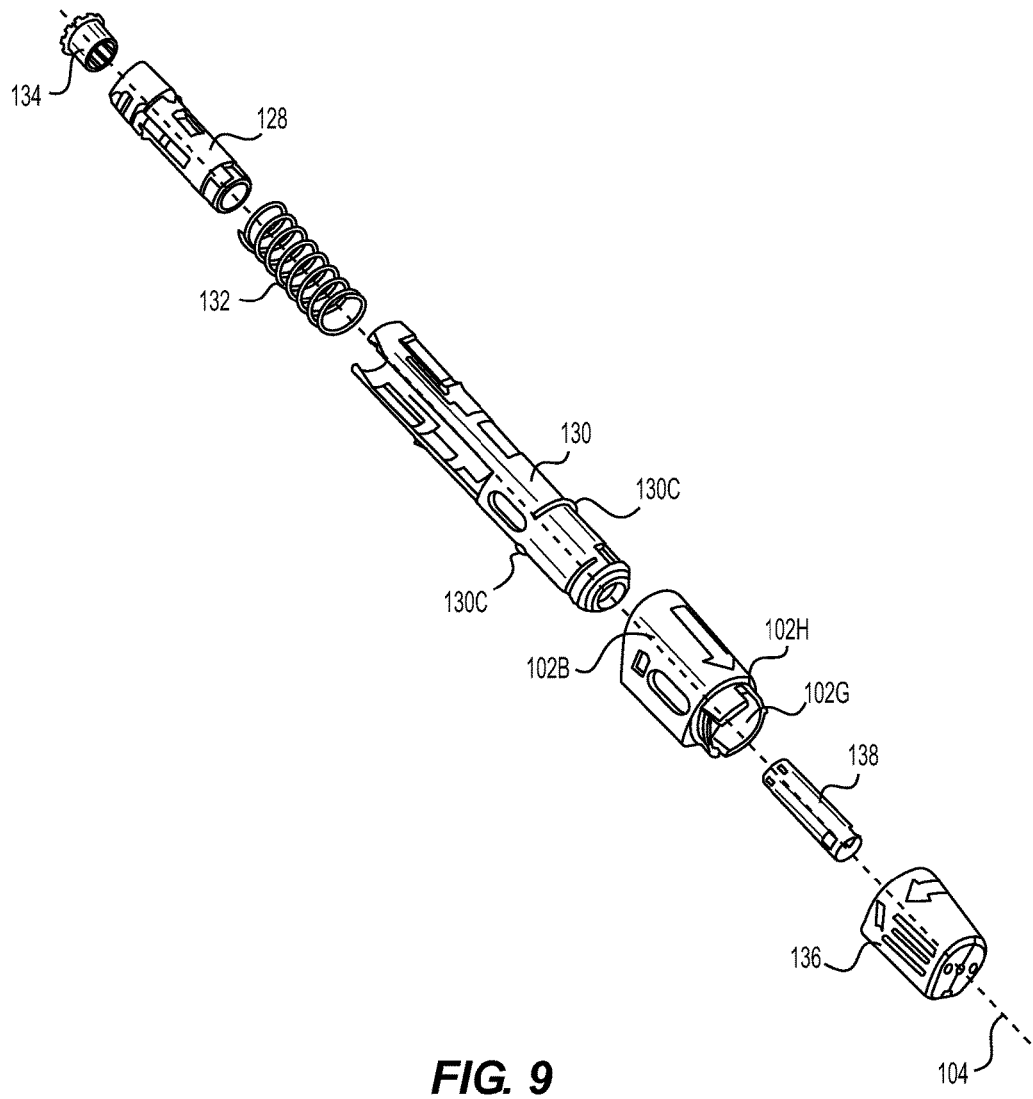
FIG. 9 is an exploded perspective front view of the second subassembly of the of the push button safety injector shown in FIG. 3.

Referring to FIGS. 3, and 9, in some embodiments, push button safety injector 100 includes a second subassembly or Module B having a plurality of internal components of push button safety injector 100. In one embodiment, push button safety injector 100 includes housing part 102B. In one embodiment, housing part 102B is configured to join to housing part 102A. In one embodiment, housing part 102B is configured join to housing part 102A by a snap fit. In one embodiment, housing part 102B is configured to join to housing part 102A by any preferred manner, including by a press fit, adhesives or welding. In one embodiment, housing part 102B includes distal opening 102G configured for receiving distal end of retractable needle guard 130 there through. In one embodiment, housing part 102B includes a stepped portion 102H near its distal end. In one embodiment, stepped portion 102H of housing part 102B is configured to engage at least one circumferential rib 130C on the outer peripheral surface of retractable needle guard 130. In one embodiment, stepped portion 102H of housing part 102B is configured to prevent further axial movement of retractable needle guard 130 in the distal direction.

Figure 8H:
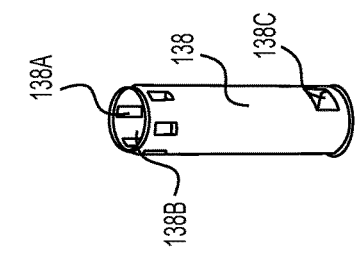
FIG. 8H is a perspective top view of a needle shield extractor for use with the second subassembly of the push button safety injector shown in FIG. 7C.
Figure 8I:
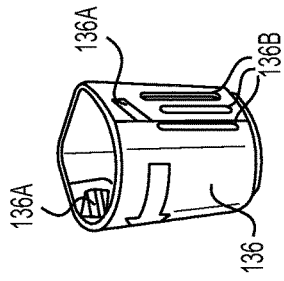
FIG. 8I is a perspective top view of a safety cap for use with the push button safety injector shown in FIG. 1.
Figure 8F:
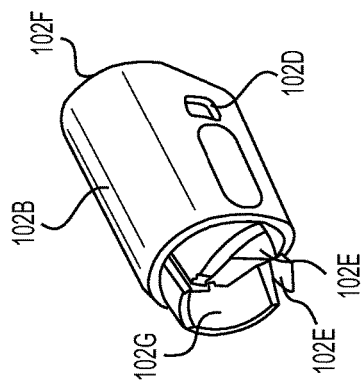
FIG. 8F is a perspective front view of a distal housing part of the push button safety injector shown in FIG. 1.
Figure 8G:
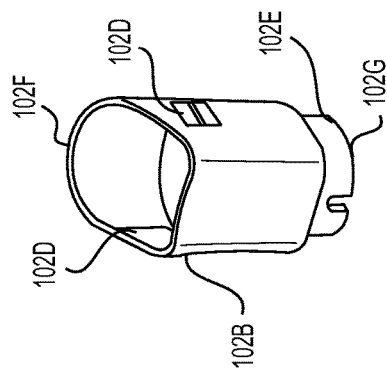
FIG. 8G is a perspective top view of the distal housing part shown in FIG. 8G.

Referring to FIGS. 8A and 9, in one embodiment, push button safety injector 100 includes sleeve member 128 positioned longitudinally along longitudinal axis 104. In one embodiment, sleeve member 128 is configured to be slidably received in retractable needle guard 130. In one embodiment, sleeve member 128 includes a body 128A having a bore 128B axially extending there through. In one embodiment, sleeve member 128 includes at least one protrusion 128C positioned on its outer peripheral surface. In one embodiment, protrusion 128C is configured to engage an axially extending slot 130B (see FIG. 8E) formed in retractable needle guard 130. In one embodiment, sleeve member 128 includes at least one locking tab 128D projecting from its outer peripheral surface. In one embodiment, locking tab 128D of sleeve member 128 is configured to be received in and through at least one mounting slot 140I of supporting member 140. In one embodiment, sleeve member 128 includes a plurality of fingers 128E at its distal end. In another embodiment, sleeve member 128 includes at least one rib 128F arranged circumferentially on its outer peripheral surface, and at least one rib 128F configured to abut distal edge of the at least one axial leg 140H of supporting member 140.

Referring to FIGS. 3, 8D, 10A and 10B, in some embodiments, push button safety injector 100 inclusion of fluid chamber 108 or the third subassembly or Module C is optional. In one embodiment, fluid chamber 108 is integrally formed within push button safety injector 100. In one embodiment, fluid chamber 108 is configured to store and dispense a liquid medicament therefrom. In one embodiment, fluid chamber 108 includes a piston 120 slidably and sealingly received there within. In one embodiment, piston 120 is configured to be longitudinally movable so as to vary the volume of fluid chamber 108. In embodiment, fluid chamber 108 includes an injection outlet 118. In one embodiment, injection outlet 118 is configured to be in fluid communication with an axial bore 108D of fluid chamber 108. In one embodiment, injection outlet 118 is configured to expel liquid medicament from fluid chamber 108. In one embodiment, injection 118 is configured to expel a fluid jet of liquid medicament with sufficient pressure to penetrate the skin of a patient. In one embodiment, injection outlet 118 includes an injection needle 122. In one embodiment, injection needle 122 is configured for piercing through a patient's skin and deliver a fluid jet of medicament 116 contained in fluid chamber 108.

Referring to FIGS. 2B and 3, in some embodiments, fluid chamber 108 is configured to be slidably received in axial bore 128B of sleeve member 128. In one embodiment, fluid chamber 108 is integrally formed within sleeve member 128. In one embodiment, fluid chamber 108 is configured to be positioned and retained by sleeve member 128. In one embodiment, fluid chamber 108 cooperates with sleeve member 128 to minimize movement of fluid chamber 108 due to injection force of injection ram 106.

Referring to FIGS. 2B and 3, in some embodiments, push button safety injector 100 includes elastomeric member 134. In one embodiment, elastomeric member 134 comprises a resilient body 134A having an axial bore 134B extending there through. In one embodiment, elastomeric member 134 includes a flange 134C positioned at its proximal edge. In one embodiment, flange 134C includes a distal facing surface having a plurality of spaced apart resilient conforming absorbing surfaces 134D arranged radially relative to longitudinal axis 104. In one embodiment, elastomeric member 134, is interposed between fluid chamber 108 and sleeve member 128. In one embodiment, elastomeric member 134 is configured to cushion fluid chamber 108. In one embodiment, flange 134C of elastomeric member 134 is configured to cushion flange 108B of fluid chamber 108.

Referring to FIGS. 8A and 9, in one embodiment, push button safety injector 100 includes sleeve member 128 configured to couple to retractable needle guard 130. In one embodiment, retractable needle guard 130 is configured to axially move relative to sleeve member 128. In one embodiment, the at least one protrusion 128C of sleeve member 128 (see FIG. 8A) is configured to engage an axially extending slot 130B (see FIG. 8E) formed in retractable needle guard 130. In one embodiment, the at least one protrusion 128C of sleeve member 128 is received in and through axially extending slot 130B of retractable needle guard 130. In one embodiment, the at least one protrusion 128C and axially extending slot 130B are configured to cooperate to limit the extent of axial movement of retractable needle guard 130 relative to sleeve member 128. In one embodiment, retractable needle guard 130, when shifted axially relative to sleeve member 128, causes the at least one protrusion 128C of sleeve member 128 to abut an inner end of axially extending slot 130B. In one embodiment, axially extending slot 130B is configured to limit lateral movement of the at least one projection 128A. In one embodiment, by limiting lateral movement of the at least one protrusion 128C, axially extending slot 130B limits angular rotation of retractable needle guard 130 about longitudinal axis 104. In one embodiment, the extent of longitudinal movement of the at least one protrusion 128C within axially extending longitudinal slot 130B defines the extent of longitudinal movement of retractable needle guard 130 relative to sleeve member 128.

Referring to FIGS. 7C and 9, in one embodiment, a biasing member 132 is interposed between sleeve member 128 and retractable needle guard 130. In one embodiment, biasing member 132 is configured to provide a biasing force for urging retractable needle guard 130 along longitudinal axis 104 toward the distal end of push button safety injector 100. In one embodiment, a biasing member 132 is interposed between the distal end of sleeve member 128 and distal end of retractable needle guard 130. In one embodiment, biasing member 132 is a spring, a piston, a flexible member, or a compressible member. In one embodiment, the plurality of fingers 128E of sleeve member 128 is configured to engage biasing member 132.

Referring to FIGS. 8C and 9, in some embodiments, Module B of push button safety injector 100 includes a elastomeric member 134 positioned longitudinally therein. In one embodiment, elastomeric member 134 of Module B includes a body 134A having an axial bore 134B extending there through. In one embodiment, elastomeric member 134 is slidably received in axial bore 128B of sleeve member 128. In one embodiment, elastomeric member 134 includes a flange 134C projecting outwardly from its proximal peripheral edge surface. In one embodiment, flange 134C of elastomeric member 134 is configured to abut the proximal edge of sleeve member 128.

Referring to FIGS. 2B, 4E and 8A, in some embodiments, push button safety injector 100 includes sleeve member 128 and supporting member 140 are coupled. In one embodiment, at least one locking tab 128D of sleeve member 128 is configured to be received in and through at least one mounting slot 140I of supporting member 140 to secure sleeve member 128 in locking engagement supporting member 140. In one embodiment, sleeve member 128 and supporting member 140 are joined by snap fitting the at least one locking tab 128D of sleeve member 128 into and through the at least one mounting slot 140I of supporting member 140. In one embodiment, sleeve member 128 and supporting member 140 are integral or joined by any preferred manner, such as a press fit, adhesives, or welding.

Referring to FIGS. 3, 10A and 10B, in some embodiments, push button safety injector 100 includes Module C positioned along longitudinal axis 104 within housing 102. In one embodiment, push button safety injector 100 includes fluid chamber 108 either contained in housing 102 or integrally formed there within. In one embodiment, fluid chamber 108 includes a body 108A having an axial bore 108D there through. In one embodiment, fluid chamber 108 is configured for storing and dispensing a liquid medicament 116 through an injection outlet 118. In one embodiment, fluid chamber 108 includes a piston 120 slidably and sealingly received there within and configured to be longitudinally movable so as to vary the volume of fluid chamber 108. In another embodiment, injection outlet 118 of fluid chamber 108 is coupled to a hollow injection needle 122 configured for piercing through a user's skin and for delivering a needle-assisted jet of liquid medicament 116 contained in fluid chamber 108. In one embodiment, injection outlet 118 of fluid chamber 108 is configured needle-free jet injection of liquid medicament 116. In some embodiments, fluid chamber 108 is prefilled with liquid medicament 116. In one embodiment, fluid chamber 108 comprises a syringe or a carpule configured to fit within housing 102. In one embodiment, fluid chamber 108 includes a flange 108B projection outwardly from its outer peripheral surface at its proximal edge. In one embodiment, flange 108B of fluid chamber 108 is configured to abut flange 134C of elastomeric member 134. In one embodiment, injection needle 122 includes a needle shield 124 having a longitudinal bore 124D configured to receive and hold injection needle 122 there within. In one embodiment, needle shield 124 includes at least one coarse surface finish 124C having a multiplicity of alternate minute recesses and ridges configured for frictional engagement.

In some embodiments, push button safety injector 100 is configured to minimize user-implemented steps to shield injection needle 122 before use or after push button safety injector 100 has been used to administer medication contained therein. In this respect, push button safety injector 100 can be used with retractable needle guard 130. In one embodiment, retractable needle guard 130 is configured to be moveable between an extended position and a retracted position. In one embodiment, retractable needle guard 130 is configured to conceal injection needle 122 in the extended position and to expose injection needle 122 in the retracted position. In one embodiment, retractable needle guard 130 can be configured to move longitudinally relative to housing 102 of push button safety injector 100 between the extended position and the retracted position. In one embodiment, retractable needle guard 130 can be configured to lock in the extended position once medication has been administered by a user of push button safety injector 100.

Figure 8E:
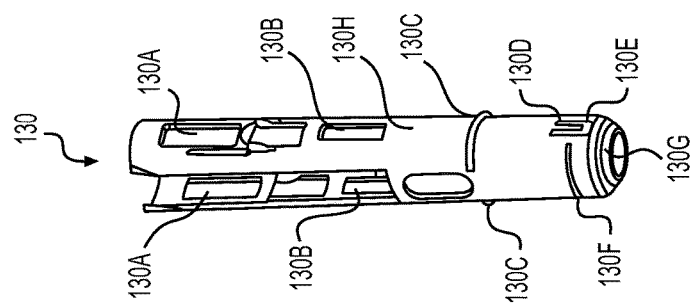
FIG. 8E is a perspective front view of a retractable needle guard of the push button safety injector shown FIG. 3.

Referring to FIGS. 4E and 8E, in one embodiment, push button safety injector 100 includes a lock-out mechanism involving the at least one flexible arm 140F of supporting member 140 and at least one lock-out slot 130A of retractable needle guard 130. In one embodiment, flexible arm 140F is configured to be moveable between an initial position and a lock-out position. In one embodiment, retractable needle guard 130 is longitudinally moveable relative to supporting member 140 when flexible arm 140F is in the initial position. In one embodiment, longitudinal movement of retractable needle guard 130 relative to supporting member 140 is restricted when flexible arm 140F is in the lock-out position. In one embodiment, the at least one flexible arm 140F of supporting member 140 is configured to be radially deflected away from longitudinal axis 104 by injection ram 106 following release of injection ram 106 by sliding member 110. In one embodiment, stepped portion 140G of flexible arm 140F is configured to engage lock-out slot 130A in retractable needle guard 130 following release of injection ram 106 by sliding member 110. In one embodiment, radially enlarged rib (collar) 106B of injection ram 106 is configured to deflect flexible arm 140F following release of injection ram 106 by sliding member 110.

Referring to FIG. 9, in some embodiments, Module B of push button safety injector 100 includes safety cap 136 coupled to housing part 102B. In one embodiment, safety cap 136 includes a needle shield extractor 138 received therein. In another embodiment, needle shield extractor 138 is slidably received in through distal opening 130G of retractable needle guard 130. In one embodiment, needle shield extractor 138 is configured to frictionally engage and retentively hold needle shield 124 to allow extraction of needle shield 124 upon removal of safety cap 136 from the distal end of housing part 102B. In one embodiment, needle shield extractor 138 is configured to mechanically lock and retentively hold needle shield 124 to allow extraction of needle shield 124 upon removal of safety cap 136 from the distal end of housing part 102B.

Figures 11A, 11B, 11C:
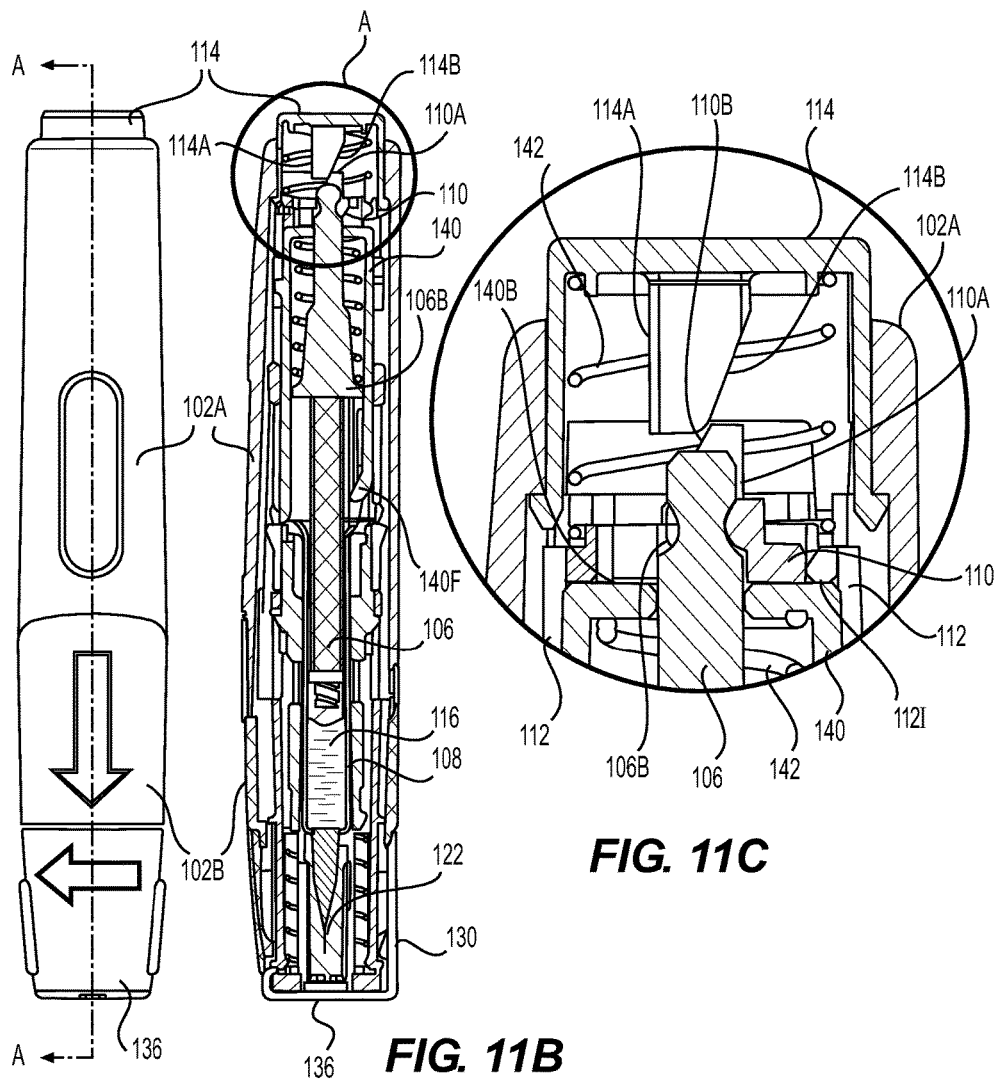
FIG. 11A is a front view of the push button safety injector shown in FIG. 1.
FIG. 11B is a cross-sectional view of the push button safety injector shown in FIG. 11A taken along line A-A.
FIG. 11C is a magnified view of Detail A of the cross-sectional view of the push button safety injector shown in FIG. 11B.

Referring to FIGS. 11A-13C, an exemplary method of use of push button safety injector 100 is shown. In FIGS. 11A-11C, push button safety injector 100 is shown when in the storage or initial and unfired state. In one embodiment, safety cap 136 is coupled to the distal end of push button safety injector 100 in the initial position. In one embodiment, push button 114 is in an initial extended position in the initial position. In one embodiment, flexible arm 140F of supporting member 140 is radially slightly biased inwardly in the initial position. In one embodiment, push button safety injector 100 is locked in the initial position meaning that push button safety injector 100 is not able to be fired by a user, for example, by manually actuating push button 114. In order for a user to operate push button safety injector 100, in one embodiment, the user needs to follow the following steps.

Figures 12A, 12B, 12C:
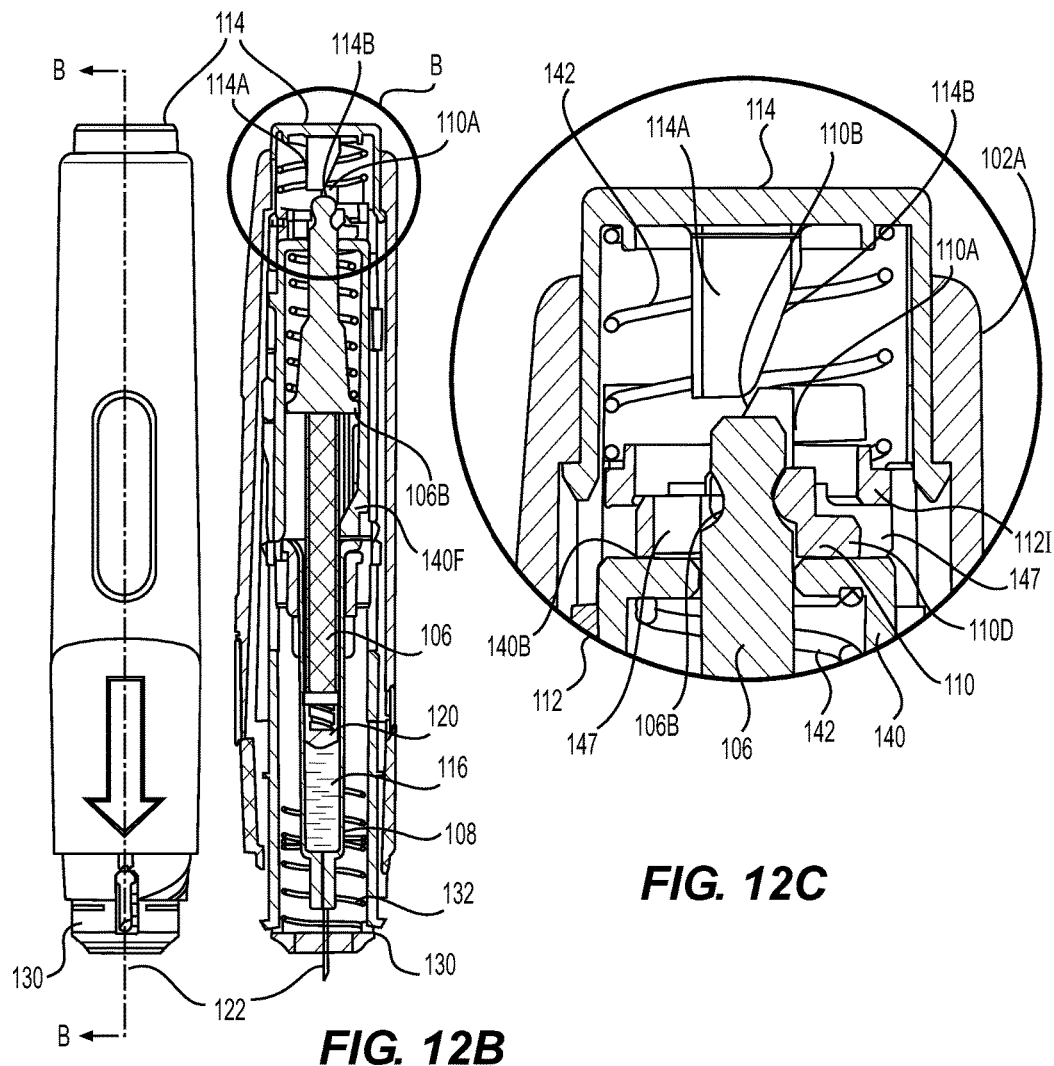
FIG. 12A is a front view of the push button safety injector shown in FIG. 1 without a safety cap, the needle guard retracted, and the safety member armed.
FIG. 12B is a cross-sectional view of the push button safety injector shown in FIG. 12A taken along line B-B.
FIG. 12C is a magnified view of Detail B of the sectional view of the push button safety injector shown FIG. 12B.

Referring to FIGS. 12A-12C, in one embodiment, in order to use the push button safety injector 100, safety member 112 is set to an armed position. In one embodiment, in order to put safety member 112 in the armed position, the user needs to first remove safety cap 136 from distal end of push button safety injector 100. In one embodiment, removal of safety cap 136 exposes distal end of retractable needle guard 130. In one embodiment, once the safety cap 136 has been removed, the user presses the exposed proximal end of retractable needle guard 130 against his or her skin at an intended injection site. In one embodiment, as the user presses retractable needle guard 130 against his or her skin, retractable needle guard 130 moves axially relative to housing 102. In one embodiment, as retractable needle guard 130 distal moves axially relative to housing 102 it exposes injection needle 122, which pierces the user's skin at the intended injection site. In one embodiment, as retractable needle guard 130 distal moves axially relative to housing 102 it causes safety member 112 to shift axially in the proximal direction. In one embodiment, by shifting safety member 112 axially in the proximal direction, safety member 112 creates a clearance space 147 between its inner peripheral surface 112I and outer peripheral surface 140B of supporting member 140. In one embodiment, clearance space 147 is configured to slidably receive at least a portion of base member 110D of sliding member 110. In one embodiment, safety member 112 is in the armed position when inner peripheral surface 112I is in spaced relation with outer peripheral surface 140B of supporting member 140. In one embodiment, when safety member 112 is in the armed position sliding member 110 is laterally moveable relative longitudinal axis 104. In one embodiment, when safety member 112 is in the armed position the confining portion of safety member 112 is axially spaced from the sliding member 110. In one embodiment, sliding member 110 is only radially moveable in the armed position. In one embodiment, the entire sliding member 110 is radially moveable in one direction in the armed position. In one embodiment, sliding member 110 is slidable at an angle in the armed position such that moving sliding member 110 includes at least a radial component. In one embodiment, when safety member 112 is in the armed position push button injector is capable of being fired. In one embodiment, once push button safety injector 100 is in the armed position the user can fire push button injector 100 by performing one or more of the steps illustrated in FIGS. 13A-13C, which will be described after the following paragraph, Referring to FIGS. 12A-12C, in one embodiment, when safety member 112 is in the armed position, flexible arm 140F of supporting member 140 is radially slightly biased inwardly. In one embodiment, when safety member 112 is in the armed position, the at least one ramped member 110A of sliding member 110 is in a complementary relation with the at least one ramped member 114A of button 114 but is not engaged with it. In one embodiment, when the safety member 112 is in the armed position, ramped surface 110B of sliding member 110 complements ramped surface 114B of push button 114 but is not engaged with it. In one embodiment, when the safety member 112 is in the armed position, the push button safety injector 100 is ready to be fired". In one embodiment, when the safety member 112 is in the armed position push button 114 is moveable axially relative to housing 102. In one embodiment, when the safety member 112 is in the armed position push button 114 is manually moveable relative to housing 102 by the user of push button safety injector 100. In one embodiment, the operation of manually firing push button safety injector 100 is as follows.

Figures 13A, 13B, 13C:
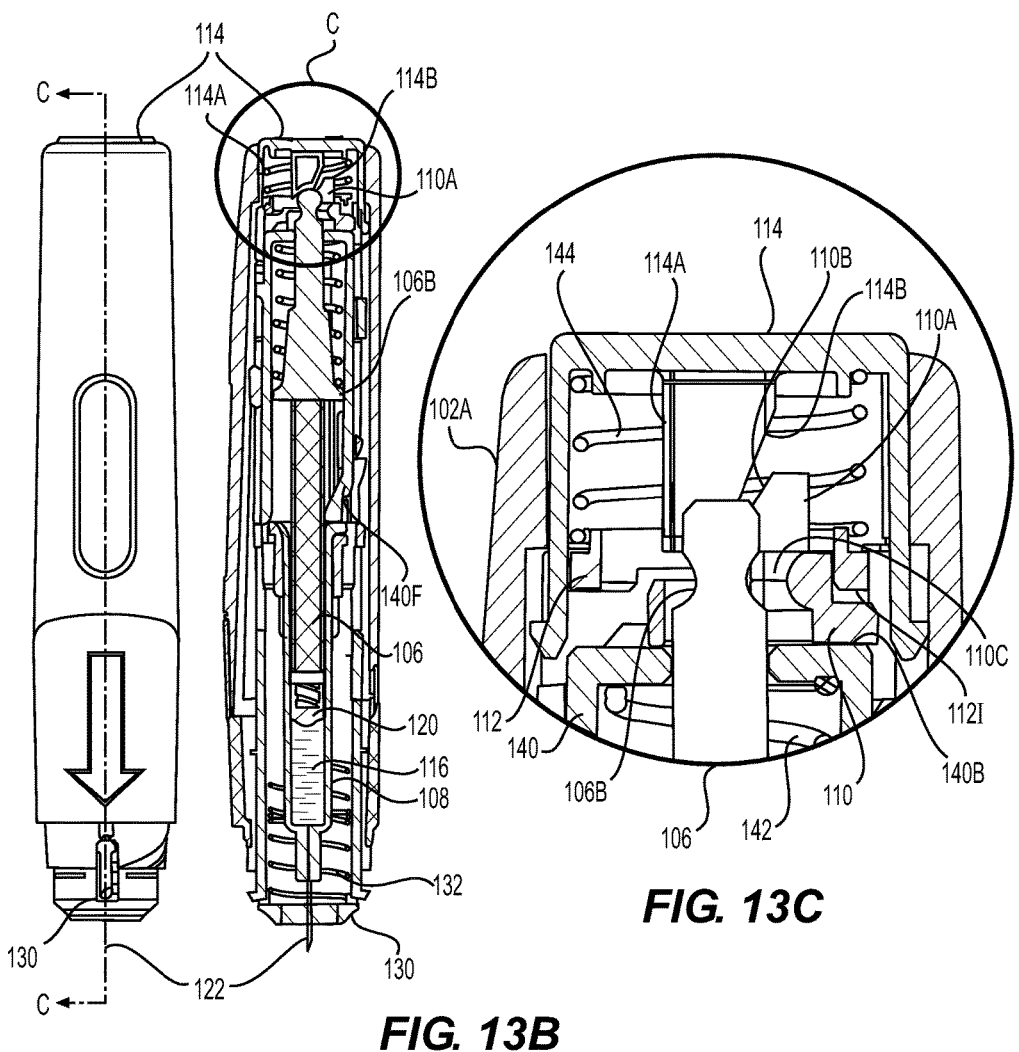
FIG. 13A is a front view of the push button safety injector shown in FIG. 1 without a safety cap, the needle guard retracted, and the push button depressed.
FIG. 13B is a cross-sectional view of the push button safety injector shown in FIG. 13A taken along line C-C.
FIG. 13C is a magnified view of Detail C of the sectional view of the push button safety injector shown in FIG. 13B.

Referring to FIGS. 13A-13C, in one embodiment, once push button safety injector 100 is in the armed position, the user of push button safety injector 100 manually applies pressure to push button 114 to shift push button 114 axially to a depressed position. In one embodiment, as push button 114 shifts axially, in response to the user's manually applied pressure, the at least one ramped member 114A engages the at least one ramped member 110A of sliding member 110. In one embodiment, ramped surface 114B of the at least one ramped member 114A comes into sliding contact with ramped surface 110B of the at least one ramped member 110A, in one embodiment, ramped surface 114B provides a sliding contact force against ramped surface 110B to urge sliding member 110 to shift laterally as the at least one ramped member 114A descends further into the interior of housing 102. In one embodiment, as sliding member 110 shifts laterally relative to longitudinal axis 104 a portion of its base member 110D intervenes in clearance space 147 between inner peripheral surface 112I and opposing outer peripheral surface 140B of supporting member 140. In one embodiment, as sliding member 110 shifts laterally relative to longitudinal axis 104, the momentum of sliding member 110 may cause ramped surface 114B to separate from ramped surface 110B. In one embodiment, ramped surfaces 114B and 110B remain in contact with one another. In one embodiment, when sliding member 110 is shifted laterally, injection ram disengages from aperture 110C of sliding member 110. In one embodiment, as injection ram disengages from aperture 110C of sliding member 110 it is released by sliding member 110. In one embodiment, as injection ram 106 is released by sliding member 110 biasing member 142 provides biasing force that urges injection ram 106 to move axially to compress fluid chamber 108 to deliver a dose of liquid medicament 116 contained in fluid chamber 108. In one embodiment, released injection ram 106 engages piston 120 and urges it to move axially toward injection outlet 118 to expel liquid medicament 116 through injection outlet 118 and into the user of push button safety injector 100. In one embodiment, when injection outlet 118 is equipped with injection needle 122, released injection ram 106 engages piston 120 and urges it to move axially toward injection outlet 118 to expel liquid medicament 116 through injection outlet 118 and injection needle 122 and into the user of push button safety injector 100.

In one embodiment, following injection of liquid medicament 116 into the user of push button safety injector 100, the user pulls retractable needle guard 130 away from his or her skin. In one embodiment, pulling retractable needle guard 130 away from the skin releases retractable needle guard 130 to extend axially. In one embodiment, biasing member 132 provides a biasing force that urges retractable needle guard 130 to shift axially to the extended position. In one embodiment, retractable needle guard 130 conceals injection needle 122 in the extended position. In one embodiment, as injection ram 106 moves axially it deflects flexible arm 140F of supporting member 140 radially outwardly. In one embodiment, enlarged rib or collar 106B of injection ram 106 confines flexible arm 140F in the deflected position. In one embodiment, as retractable needle guard 130 extends axially, deflected flexible arm 140F of supporting member 140 engages lock-out slot 130A. In one embodiment, stepped portion 140G of flexible arm 140F is received in and through lock-out slot 130A. In one embodiment, by engaging lock-out slot 130A flexible arm 140F precludes any axial movement of retractable needle guard 130 relative to housing 102. In other words, in one embodiment, following injection, push button safety injector 100 enters a lock-out state which precludes the user from reusing push button safety injector 100. In one embodiment, when push button safety injector 100 is in the lock-out state it minimizes exposure of its user or others with access to push button safety injector 100 to the possibility of accidental needle sticks and other risks associated with exposure to residual liquid medicament 116, bodily fluids, and/or blood borne pathogens during handling and/or disposal of push button safety injector 100.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the Figs. and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A push button safety injector comprising:
a housing having a proximal end, a distal end spaced from the proximal end, and a longitudinal axis;
an injection ram positioned along the longitudinal axis and configured to actuate a fluid chamber, the injection ram being biased toward the distal end in an initial position;
a sliding member retaining the injection ram in the initial position;
a safety member confining radial movement of the sliding member in the initial position and allowing radial movement of the sliding member in an armed position; and
a button moveable between an initial extended position and a depressed position, the button being engagable with the sliding member and configured to move the sliding member radially in the armed position, wherein the sliding member releases the injection ram when the button is in the depressed position,
wherein movement of the button from the extended position to the depressed position is configured to cause the radial movement of the sliding member.

2. The push button safety injector of claim 1 further comprising:
a fluid chamber configured to store a liquid medicament.

3. The push button safety injector of claim 2, further comprising:
a piston slidably and sealingly received within the fluid chamber, the piston configured to be longitudinally movable in the fluid chamber.

4. The push button safety injector of claim 2, wherein the fluid chamber includes an injection outlet.

5. The push button safety injector of claim 4 further comprising:
a retractable needle guard configured to be moveable longitudinally relative to the fluid chamber between an extended position, in which the retractable needle guard extends along at least a length of the injection outlet, and a retracted position, in which the retractable needle guard exposes at least a portion of the length of the injection outlet.

6. The push button safety injector of claim 5 further comprising:
a sleeve member interposed between the fluid chamber and the retractable needle guard.

7. The push button safety injector of claim 5, wherein the retractable needle guard is biased toward the distal end of the housing in the extended position.

8. The push button safety injector of claim 4, wherein the injection outlet comprises an injection needle configured to deliver the liquid medicament in the fluid chamber to a user.

9. The push button safety injector of claim 2, wherein the fluid chamber includes a prefilled syringe or carpule.

10. The push button safety injector of claim 2 further comprising:
a sleeve member configured to at least one of position the fluid chamber and minimize movement of the fluid chamber due to injection force of the injection ram.

11. The push button safety injector of claim 10, wherein the sleeve member is mounted within the housing and configured to support a biasing member interposed between the sleeve member and a needle guard.

12. The push button safety injector of claim 10 further comprising:
an elastomeric member interposed between the fluid chamber and the sleeve member.

13. The push button safety injector of claim 1, wherein the sliding member includes an aperture extending longitudinally there through.

14. The push button safety injector of claim 13, wherein the aperture includes a slot and a hole, wherein the slot is in communication with the hole.

15. The push button safety injector of claim 14, wherein the slot has a width and the hole has a diameter, wherein the width of the slot is less than the diameter of the hole.

16. The push button safety injector of claim 14, wherein the injection ram includes an engagement recess configured to engage the slot of the sliding member when the injection ram is in the initial position, the engagement recess configured to disengage from the slot of the sliding member when the safety member is in the armed position.

17. The push button safety injector of claim 1 further comprising:
a safety cap removably coupled to the distal end of the housing, the safety cap configured to prevent movement of the safety member into the armed position.

18. The push button safety injector of claim 17, wherein the safety cap is configured to receive at least a portion of a retractable needle guard.

19. The push button safety injector of claim 5 further comprising:
a lock-out mechanism having at least one flexible arm formed in a supporting member and at least one slot formed in the retractable needle guard, the flexible arm being configured to be moveable between an initial unlocked position, which allows longitudinal movement of the needle guard relative to the supporting member, and a lock-out position, in which the at least one flexible arm is in a locking engagement with the at least one slot of the retractable needle guard, wherein the retractable needle guard is locked in the extended position following injection.

20. The push button safety injector of claim 1, wherein the safety member is moved relative to the sliding member between the initial position and the armed position.

* * * * *